US006287257B1

(12) United States Patent
Matichuk (10) Patent No.: US 6,287,257 B1
(45) Date of Patent: Sep. 11, 2001

(54) METHOD AND SYSTEM FOR CONFIGURING A MEDICAL DIAGNOSTIC ULTRASOUND IMAGING SYSTEM

(75) Inventor: Chris E. Matichuk, Sunnyvale, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/343,076

(22) Filed: Jun. 29, 1999

(51) Int. Cl.$^7$ ........................................................ A61B 8/00
(52) U.S. Cl. ........................................................ 600/437
(58) Field of Search ........................................ 600/437, 443, 600/447, 300; 128/916

(56) References Cited

U.S. PATENT DOCUMENTS 5,851,186 * 12/1998 Wood et al. ........................ 600/437

OTHER PUBLICATIONS

"Dicom Image Manager"; Brochure by Dicomit Imaging Systems Corp.; (2 pages).
Ali Ultrapacs User's Guide, pp. 1–v, 7, and 2–1 to 2–6, (Aug. 20, 1998).
Ali Data Exchange Server 1.0—Dicom Comformance Statement, HTTP://www.alitech.com/DXS—Dicom.HTML, 7 pages, (Apr. 16, 1997).
Ali Ultrapacs 3.0—Improve Productivity, HTTP://www.alitech.com/proctvty.HTML (1 page).
Ali Ultrapacs 3.0—HL7: Health Level 7, HTTP://www.alitech.com/HL7.HTML, (1 page).
Health Level Seven Overview, 7 pages.
HL7 Image Management SIG, 8 pages. (Apr. 23–25, 1996).
Dicom Supplement 10–Basic Worklist Management, 6 pages, (Aug. 10, 1995).
Dicom Part 3 Addendum—Basic Worklist Management, 10 pages, (Aug. 10, 1995).
Dicom Parts 4 and 6 Addendum—Basic Worklist Management, 26 pages, (Aug. 10, 1995).
Dicom Annex K—Basic Worklist Management Service, pp. 217–231, (Draft Standard 1998).

* cited by examiner

Primary Examiner—Francis J. Jaworski
(74) Attorney, Agent, or Firm—Brinks Hofer Gilson & Lione (57) ABSTRACT

The preferred embodiments described herein provide a method and system for configuring a medical diagnostic ultrasound imaging system. In one preferred embodiment, an ultrasound system analyzes patient information from a hospital information system to determine what ultrasound settings are appropriate. The ultrasound system can then automatically configure itself with these settings or can present a plurality of suggested settings to a sonographer for selection. In another preferred embodiment, the ultrasound system uses patient information received from the hospital information system to automatically configure and/or populate a patient demographic worksheet.

47 Claims, 4 Drawing Sheets

| NAME | |
|---|---|
| ID | |
| STUDY TYPE | |
| PHYSICIAN | |

Fig. 5

| NAME | ARIA BERNARDI |
|---|---|
| ID | 123-45-6789 |
| STUDY TYPE | PED. |
| PHYSICIAN | DR. SZANDRA |

Fig. 6

| NAME | ARIA BERNARDI |
|---|---|
| ID | 123-45-6789 |
| STUDY TYPE | PED. |
| PHYSICIAN | DR. SZANDRA |
| DATE OF BIRTH | JUNE 4, 1999 |

METHOD AND SYSTEM FOR CONFIGURING A MEDICAL DIAGNOSTIC ULTRASOUND IMAGING SYSTEM

BACKGROUND

To configure an ultrasound system for an examination of a patient, a sonographer analyzes information about the patient to be examined in order to determine what ultrasound settings to use. The sonographer then manually configures the ultrasound system with these settings. One source of patient information is a hospital information system ("HIS") or a radiology information system ("RIS"). In some clinical environments, information about a patient to be examined is entered into a HIS/RIS when the examination is scheduled. At the time of the examination, the sonographer can access this information via a HIS/RIS terminal. The sonographer can then interpret the relevant patient information and configure the ultrasound system accordingly. For example, the sonographer can decide which system presets or ultrasound settings to use by considering the age, weight, and condition of the patient to be studied. The sonographer can also use information stored on a HIS/RIS to determine which fields (e.g., age, sex, weight, etc.) should be added to a patient demographic worksheet and to manually populate these fields.

Recently, some ultrasound systems have been provided with the capability of interfacing with a HIS/RIS so that a sonographer can retrieve and view patient information from the ultrasound system. While this advance makes accessing the HIS/RIS more convenient for the sonographer, the sonographer still faces the sometimes difficult and time consuming task of interpreting the retrieved patient information and manually configuring the ultrasound system or patient demographic worksheet.

There is a need, therefore, for a method and system for configuring a medical diagnostic ultrasound imaging system that will overcome the disadvantages described above.

SUMMARY

The present invention is defined by the following claims, and nothing in this section should be taken as a limitation on those claims.

By way of introduction, the preferred embodiments described below provide a method and system for configuring a medical diagnostic ultrasound imaging system. In one preferred embodiment, an ultrasound system analyzes patient information from a hospital information system to determine what ultrasound settings are appropriate. The ultrasound system can then automatically configure itself with these settings or can present a plurality of suggested settings to a sonographer for selection. In this way, the ultrasound system of this preferred embodiment reduces or eliminates the sometimes difficult and time consuming tasks of manually interpreting retrieved patient information and manually configuring the ultrasound system. In addition to reducing the overhead time required to start a new study, the preferred ultrasound system also reduces costs while increasing the quantity of studies that can be performed.

In another preferred embodiment, the ultrasound system uses patient information received from the hospital information system to automatically configure and/or populate a patient demographic worksheet. This preferred embodiment offers time-saving and error-reduction benefits and increases the consistency of information acquired throughout all hospital departments, which can lead to an improvement of overall hospital workflow and improved diagnosis.

The preferred embodiments will now be described with reference to the attached drawings.

DETAILED DESCRIPTION OF THE PRESENTLY PREFERRED EMBODIMENTS

Figure 1:
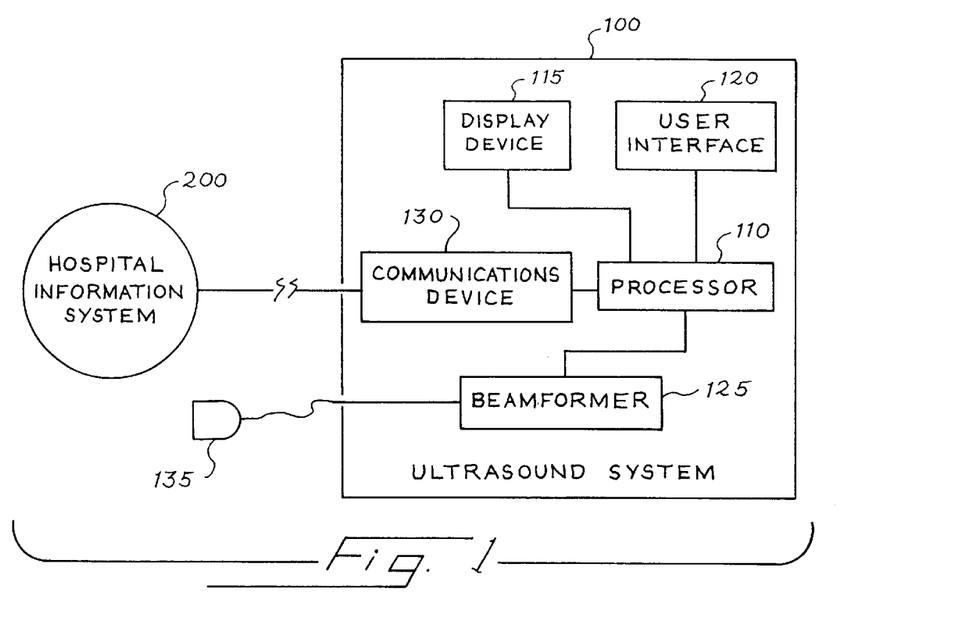
FIG. 1 is an illustration of a diagnostic medical ultrasound imaging system of a preferred embodiment coupled with a hospital information system.

Turning now to the drawings, FIG. 1 is an illustration of a medical diagnostic ultrasound imaging system 100 of a preferred embodiment. The ultrasound system 100 comprises a processor 110 coupled with a display device 115, a user interface 120, a beamformer 125, a communications device 130, and a transducer 135. It is important to note that, for simplicity, the ultrasound system 100 of FIG. 1 contains only some of the many possible components that can comprise an ultrasound system and that additional components can be used. During an ultrasound examination of a patient, the beamformer 125 applies a voltage to the transducer 135 to cause it to vibrate and emit ultrasonic energy to the patient. Voltages are created by the transducer 135 when ultrasonic energy reflected by structures in the patient's tissue impinge on the transducer 135. These returned voltages are analyzed to form an image on the display device 115.

The ultrasound system 100 also has a communications device 130 that couples the ultrasound system 100 with a hospital information system 200. As used herein, the term "coupled with" means directly coupled with or indirectly coupled with through one or more components. Also as used herein, the term "communications device" is intended to cover any device that can be used by the ultrasound system 100 to receive patient information from a hospital information system 200. Examples of communications devices include, but are not limited to, modems, network connectors (such as an Ethernet or TCP/IP connector), and wireless communications devices.

For simplicity, the term "hospital information system" in this specification and the following claims is intended broadly to encompass any depository of information that holds patient information. Depending on the system's environment, a "hospital information system" can be a Hospital Information System ("HIS") (e.g., a computer system that handles and stores data related to operations, patient billing, patient clinical records, and reporting), a Radiology Information System ("RIS") (e.g., a computer system with multiple terminals that allows patient scheduling, billing, reporting, and demographic data storage), a Picture Archive and Communications Systems ("PACS") (e.g., a department- or hospital-wide computer system that transmits and reviews images from diagnostic imaging modalities), or any other primary or intermediary (secondary) system that stores and/or transmits patient information.

"Patient information" is intended to broadly refer to any information that is or can be stored and processed by a hospital information system. Patient information can include demographic information (e.g., patient name, patient id, etc.) and information regarding a scheduled procedure (e.g., the description, location, date, time, and identifier for a scheduled procedure). Patient information can also include information that can be stored in accordance with the Health Level 7 ("HL7") standard or the Digital Imaging and Communications in Medicine ("DICOM") Modality Worklist structure. For example, patient information can include information used in conjunction with some or all of the attributes listed in Table K. 6-1 of the DICOM 3.0 Modality Worklist Information Model. These attributes include scheduled procedure step, requested procedure, imaging service request, visit identification, visit status, visit relationship, visit admission, patient relationship, patient identification, patient demographic, and patient medical information.

Figure 2:
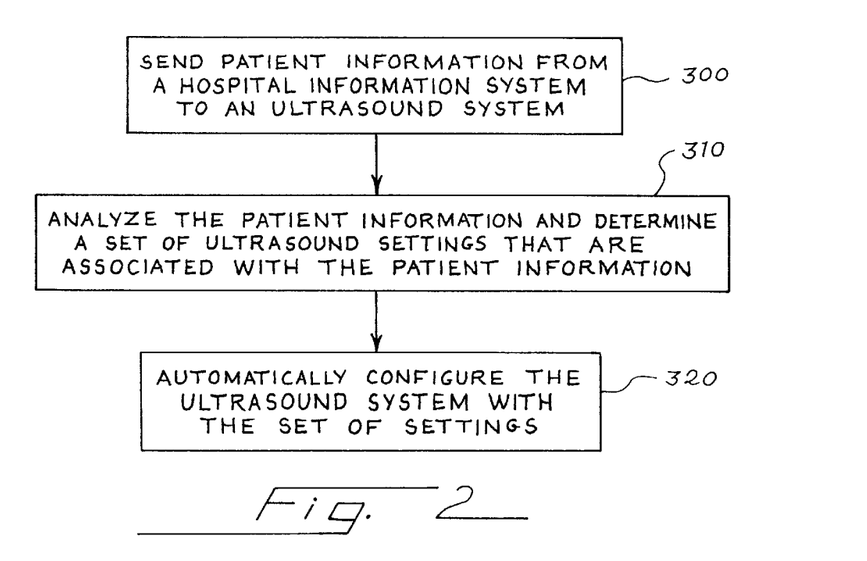
FIG. 2 is a flow chart of a method of a preferred embodiment for automatically configuring an ultrasound system.

FIG. 2 is a flow chart of a method of a preferred embodiment illustrating how the ultrasound system 100 is automatically configured. First, patient information is sent from the hospital information system 200 to the ultrasound system 100 via the ultrasound system's communication device 130 (block 300). It is important to note that patient information is sent to the ultrasound system 100 when the information is either pushed or pulled from the hospital information system 200. For example, the hospital information system 200 can send patient information to the ultrasound system 100 in response to a query from the ultrasound system 100 (i.e., when the information is pulled from the system 200) or can automatically send patient information to the ultrasound system 100 in response to a triggering event, such as the scheduling of a patient (i.e., when the information is pushed from the system 200). Patient information is also sent to the ultrasound system 100 from the hospital information system 200 when patient information is transferred from the hospital information system 200 to the ultrasound system 100 via removable/portable media (e.g., a MO disc).

Second, the ultrasound system's processor 110 analyzes the received patient data and determines a set of ultrasound settings that are associated with the patient information sent from the hospital information system 200 (block 310). Then, the processor 110 automatically configures the ultrasound system 100 with the set of ultrasound settings (block 320). As used herein, the term "set" shall refer to a set with one or more than one member, and an ultrasound setting can include any setting or parameter that can be adjusted or configured on the ultrasound system and can include system or user presets.

Because the processor 110 analyzes and automatically configures the ultrasound system 100, the ultrasound system of this preferred embodiment reduces or eliminates the sometimes difficult and time consuming task of manually interpreting retrieved patient information and manually configuring the ultrasound system. In addition to reducing the overhead time required to start a new study, this preferred ultrasound system 100 also reduces costs while increasing the quantity of studies that can be performed. The following are some applications of this preferred method. It is important to note that these are merely examples and are not intended to limit the invention in any way.

In one example, the processor 110 analyzes patient information from the hospital information system 200 to determine what type of study is to be performed and which ultrasound settings should be used. For example, if the patient information indicates that an obstetrics examination will be performed, the processor 110 can select the appropriate scanning application and ultrasound settings. In another example, the patient information received from the hospital information system 200 contains information about the patient's age and weight. In this application, the processor 110 analyzes the age and weight information to determine whether to use tissue harmonic imaging. For example, after learning that the patient is 12 years old and is 200 pounds, the processor 110 can automatically configure the ultrasound system 100 for tissue harmonic imaging.

The patient information can also contain data relating to the condition of the patient or to the reason for a diagnosis (e.g., a "CPT" code in the "Reason for Diagnosis" field in a Scheduled Study record). If the patient information indicates that the patient has a heart problem and is scheduled for a stress test, for example, the processor 110 can determine that a drug stress test (instead of an exercise stress test) should be administered and configure the system 100 accordingly. Similarly, if the patient information indicates that the patient has right lower extremity pain after walking one block, the processor 110 could rule out a narrowing of the arteries and suggest that an arterial study be performed and that Color Doppler and Pulsed Waved Spectral Doppler settings be used.

In addition to patient-related data, the processor 110 can also use other forms of patient information to configure the system 100. For example, the processor 110 can choose pre-set ultrasound settings that are preferred by a sonographer scheduled to perform a study. In this way, the system 100 will be customized for the sonographer, and the sonographer will not be distracted by a perceived inferior configuration or need to spend time reconfiguring the system to his preferences. As another example, some physicians or hospitals have particular preferences as to how data is acquired by the ultrasound system 100. For instance, for OB studies, some physicians may use a different set of OB equations than the standard configuration. If the reading physician or referring site is indicated in the patient information received from the hospital information system 200, the processor 100 can configure the system 100 accordingly.

In an alternate embodiment, instead of automatically configuring the system 100, the processor 110 can present several suggested ultrasound settings to the user of the ultrasound system 100. For example, the processor 110 can visually display the suggestions on the system's display device 115 or announce the suggestions via a speaker. Using the system's user interface 120 (e.g. a keyboard, trackball, mouse, microphone, etc.), a user selects one of the suggestions, and the processor 110 configures the system 100 with the ultrasound settings associated with the selection. One advantage associated with this alternative is that the sonographer can be alerted to special features of the system 100 that could add value to the study. For example, given the age and weight of a patient, the processor 110 can provide the sonographer with the option of using a tissue harmonic imaging mode. As another example, information about when the last study was performed for the same patient reporting a particular condition can be used by the processor 110 to alert and offer the sonographer suggestions.

Figure 3:
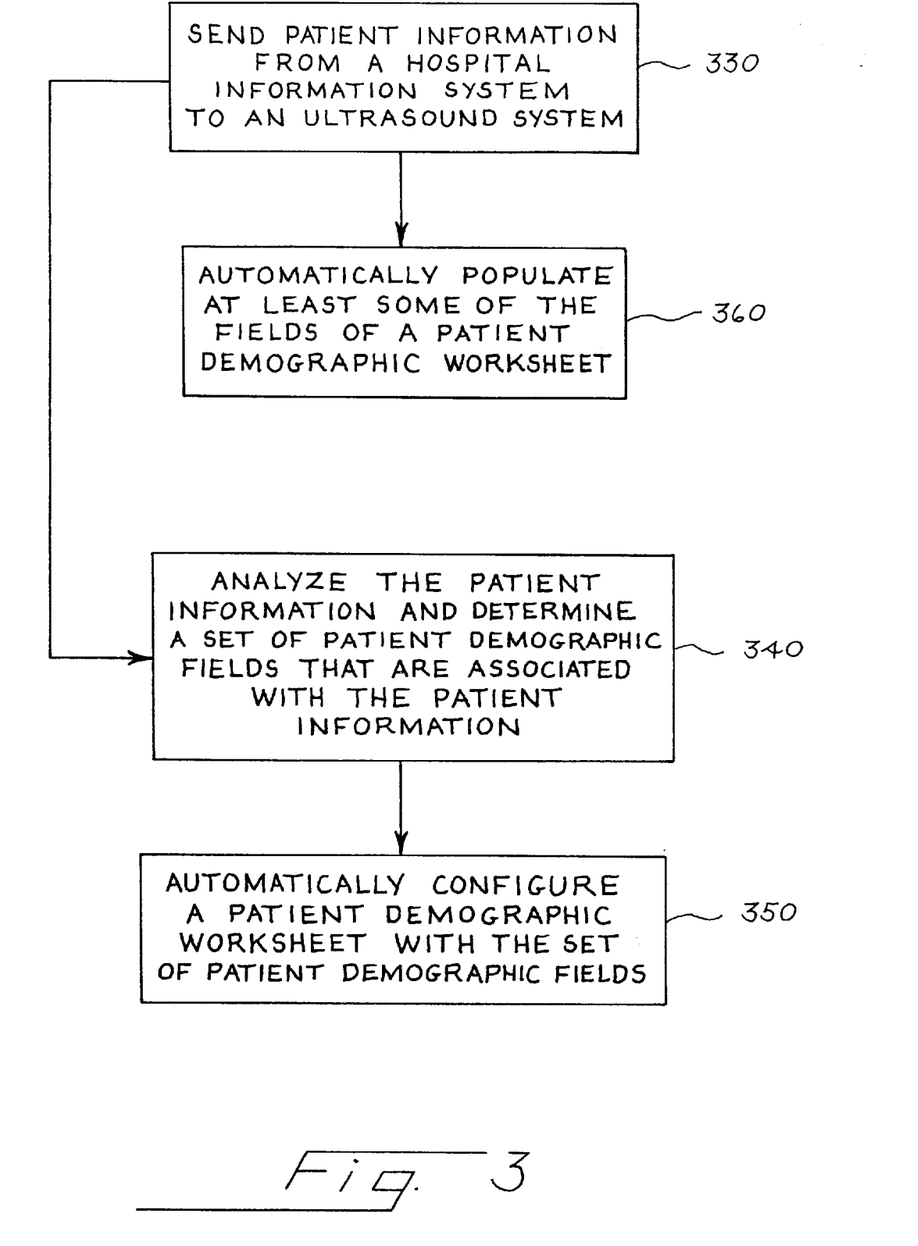
FIG. 3 is a flow chart of a method of a preferred embodiment for automatically configuring a patient demographic worksheet and/or populating fields in a patient demographic worksheet.

In another preferred embodiment, the ultrasound system 100 uses patient information received from the hospital information system 200 to automatically configure a patient demographic worksheet and/or automatically populate some or all of the fields of a patient demographic worksheet, as shown in the flow chart of FIG. 3. First, patient information is sent from the hospital information system 200 to the ultrasound system 100 (block 330). Next, the processor 110 determines a set of patient demographic fields that are associated with the patient information sent from the hospital information system 200 (block 340). Then, the processor 110 automatically configures a patient demographic worksheet with the set of patient demographic fields (block 350). The patient demographic worksheet can then be displayed on the display device 115, and the user can populate the fields of the worksheet using the user interface 130. Additionally or alternatively, the processor 110 can automatically populate at least some of the fields of the patient demographic worksheet with at least some of the patient information sent from the hospital information system 200 (block 360).

Figure 4:
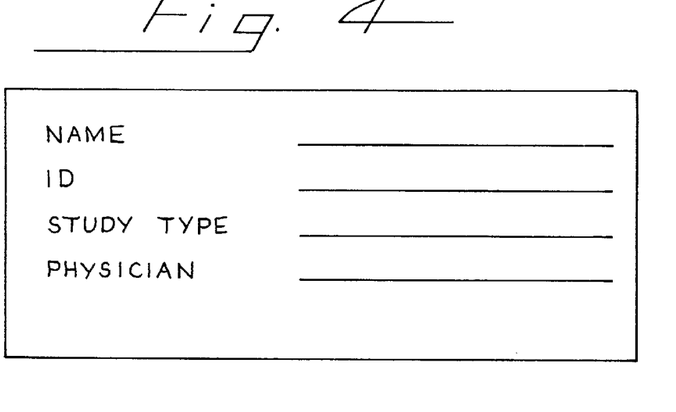
FIG. 4 is an illustration of a patient demographic worksheet of a preferred embodiment.
Figure 5:
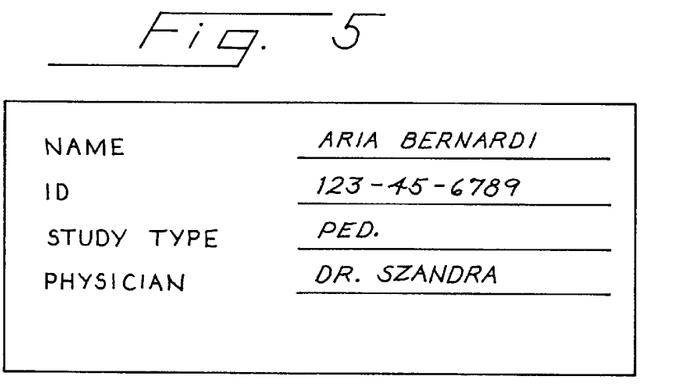
FIG. 5 is an illustration of a patient demographic worksheet of a preferred embodiment in which the fields of the worksheet are automatically populated.
Figure 6:
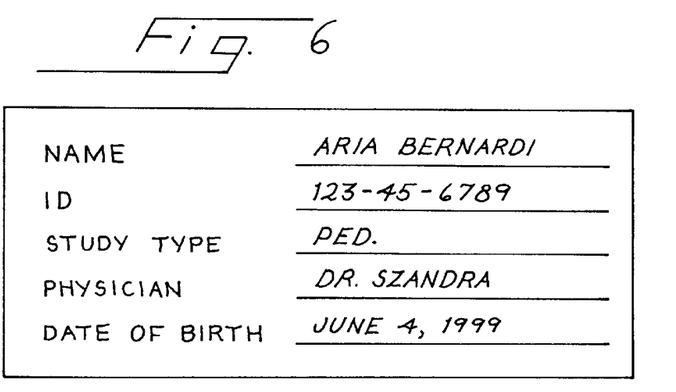
FIG. 6 is an illustration of a patient demographic worksheet of a preferred embodiment in which the fields of the worksheet are automatically configured.

FIGS. 4–6 are patient demographic worksheets that illustrate this preferred embodiment. FIG. 4 is an illustration of a patient demographic worksheet with the following fields: name, ID, study type, and physician. If the patient information received by the processor 110 contains information relating to these fields, the processor 110 can populate these fields with the relevant data, as shown in FIG. 5. Further, if the patient information contains additional information, the processor 110 can create fields for the additional information and configure the worksheet accordingly. For example, if the patient information contains the patient's date of birth, the processor 110 can configure the worksheet with a date-of-birth field, as shown in FIG. 6. As another example, if the patient information indicates that an obstetrics examination will be performed, the processor 110 can determine that the patient is female and enter "female" in the sex field of the patient demographic worksheet. The processor 110 can also add the last menstrual period ("LMP") and expected date of delivery ("EDD") fields because those fields are needed in an obstetrics study. In addition to time-saving and error-reduction benefits, automatic population of configured fields increases the consistency of information acquired throughout all hospital departments, which can lead to an improvement of overall hospital workflow and improved diagnosis.

Figure 7:
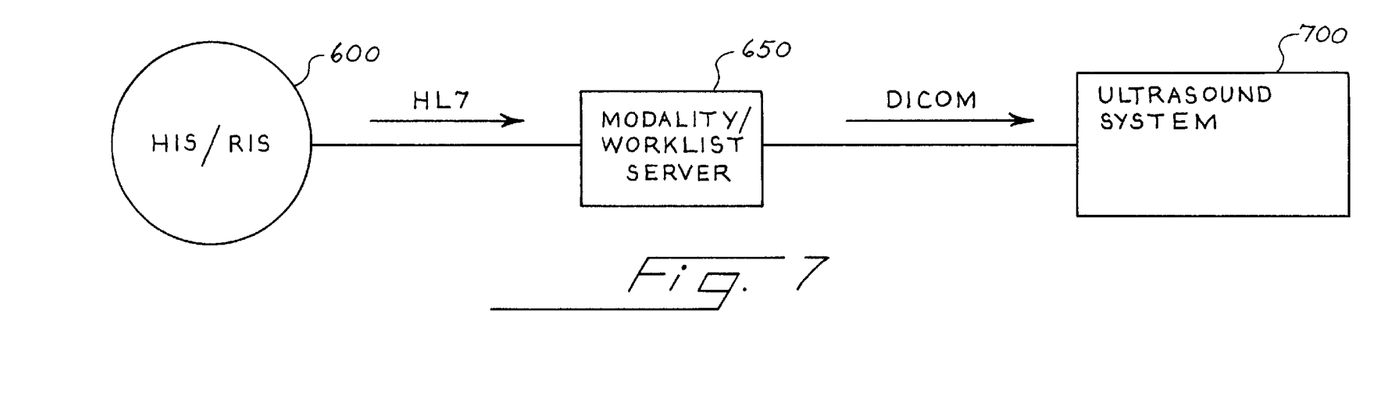
FIG. 7 is an illustration of a diagnostic medical ultrasound imaging system of a presently preferred embodiment coupled with a modality worklist server, which is coupled with a HIS/RIS.

FIG. 7 is an illustration of an implementation of one presently preferred embodiment. In this implementation, the ultrasound imaging system 700 is configured in accordance with the Digital Imaging and Communications in Medicine ("DICOM") Modality Worklist standard, and the hospital information system is a HIS/RIS 600 storing patient information in accordance with the Health Level 7 ("HL7") standard. The DICOM Modality Worklist is a structure to present information related to a particular set of tasks and specifies particular details for each task. For example, a worklist can present information about scheduled imaging procedure to an ultrasound system. HL7 is oriented towards the clinical and administrative aspects of a medical enterprise and allows disparate systems to intercommunicate freely. HL7 can communicate patient information comprising, for example, patient medical history and demographics, encounter and visit histories, admit/discharge/transfer and patient tracking information, scheduling and referrals, orders and results (measurements, observations, impressions, reports), pharmacy and diet information, and census information.

In operation, when a patient is scheduled for an ultrasound study, information is entered into the HIS/RIS 600 to create a Scheduled Study on the HIS/RIS 600. A Scheduled Study comprises both Patient Demographic Information (such as the patient's name, ID, and other related information about the patient) and Scheduled Procedure Step Information (such as the description, location, date, time, and a unique identifier). The Scheduled Study is then sent from the HIS/RIS 600 to a Modality Worklist Server 650. The Modality Worklist Server 650 (also known as a "broker") is an interface between HL7-compliant HIS/RIS 600 and DICOM-compliant ultrasound system 700.

When the patient is admitted to the examination room, the sonographer queries the Modality Worklist Server 650 from the ultrasound system 700 and selects the Scheduled Study for the admitted patient. The Modality Worklist Server 650 then returns the DICOM 3.0-compliant Scheduled Study information to the ultrasound system 700. As described above, the ultrasound system 700 analyzes the Scheduled Study information (or additional information from the HIS/RIS 600, such as patient history or information from related prior studies) to automatically configure the ultrasound system 700 (or recommend suggested settings to the sonographer). Additionally or alternatively, the ultrasound system 700 can automatically configure a patient demographic worksheet and/or automatically populate at least some of the fields of a patient demographic worksheet. Accordingly, by using Scheduled Study information retrieved from a networked server, the tasks required to configure an ultrasound system for a new study are reduced.

The following example illustrates the use of the above-described ultrasound system 700. In this example, the ultrasound system 700 is pre-configured with Study Types OB and OB-LT. If a patient is scheduled for an OB examination, the Scheduled Study created on the HIS/RIS 600 indicates that Scheduled Procedure Step is an OB examination. When the Scheduled Study is sent from the HIS/RIS 600 to a Modality Worklist Server 650, the Modality Worklist Server 650 translates this HL7 Scheduled Procedure Step into the DICOM Modality Worklist standard by placing the abbreviation OB into the DICOM element "Scheduled Procedure Step Description" (i.e., tag 0x0040,0x0007).

When the Scheduled Study information is sent from the Modality Worklist Server 650 to the ultrasound system 700, the ultrasound system's processor analyzes the Scheduled Study information to select the appropriate Study Type. The ultrasound system 700 can, for example, map the Study Description field of the Scheduled Study information to the Study Type field by using one-to-one mapping, a pre-configured mapping table, algorithmic mapping, or any combination thereof. An example of an algorithmic mapping is a Closest Match algorithm, which is particularly useful where more than one Study Type partially matches, but some or one Study Type matches closer than the others. To find the closest match using this algorithm, all of the non-alphanumeric characters of both the Scheduled Study information and the Study Type are removed, and the remaining characters are changed to uppercase. For example, a Scheduled Study abbreviation of OBLT would match to OB-LT. If, however, the Scheduled Study abbreviation of OBRT were received, the closest match would be OB.

As a further illustration of this algorithm, exemplary predefined Study Types of a preferred ultrasound system are listed in Table 1, and Scheduled Procedure Step Descriptions and their corresponding mapped Study Types are shown in Table 2.

TABLE 1

| Study Types |
|---|
| USAB |
| USABX |
| US AB |
| USAB RT |

TABLE 2

| Scheduled Procedure Step Description | Mapped Study Type |
|---|---|
| USAB | USAB |
| USABX | USABX |
| USABY | USAB |
| US:AB | US AB |
| USA | DEFAULT STUDY TYPE |
| USANA | DEFAULT STUDY TYPE |
| USAB/LT | USAB |
| USAB/RT | USAB RT |
| USABX/LT | USABX |
| USABNA/LT | DEFAULT STUDY TYPE |

It is important to note that any method of analyzing the incoming information to select a set of ultrasound settings can be used in addition to or instead of the methods described above. It is also important to note that any of the various aspects of the preferred embodiments can be used alone or in combination. Additionally, while it is preferred that ultrasound system perform the methods described above using any appropriate software and that the ultrasound system comprise the necessary hardware components to run the software, it is important to note that any appropriate hardware, analog or digital, and any appropriate software language can be used. Additionally, the methods described above can be implemented exclusively with hardware.

Figure 8:
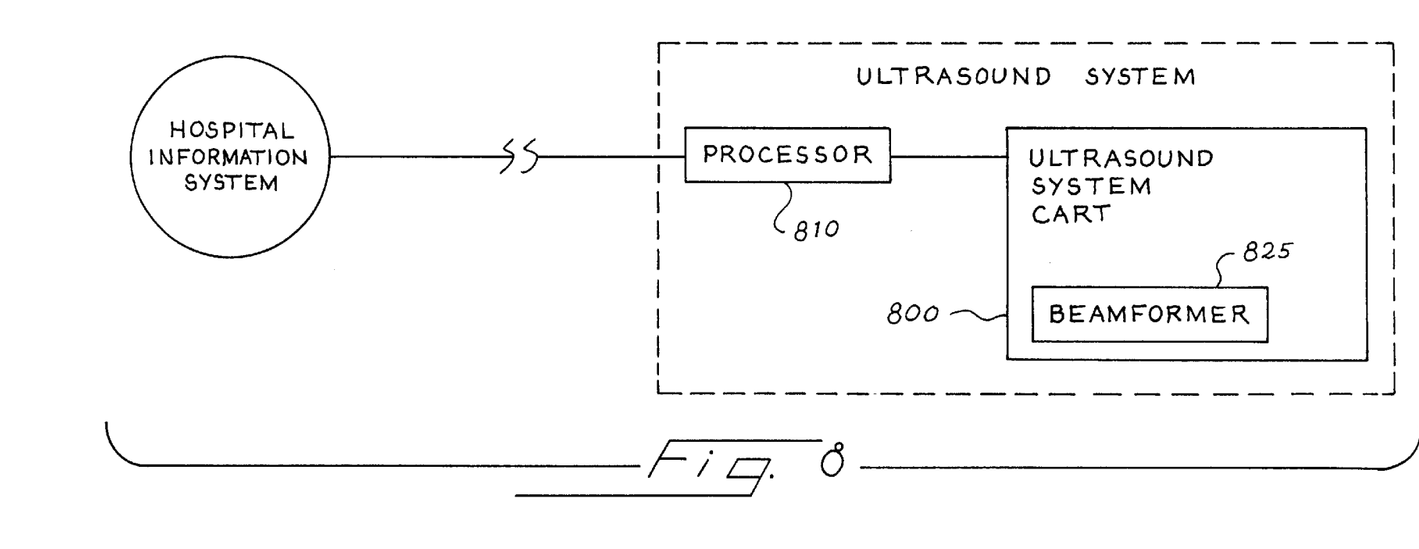
FIG. 8 is an illustration of a diagnostic medical ultrasound imaging system of another preferred embodiment in which the ultrasound system's processor that is coupled with a hospital information system is externally located from an ultrasound system cart that houses a beamformer.

Further, while the term "processor" has been used above to describe the component of the ultrasound system that analyzes patient information from a hospital information system and configures the ultrasound system accordingly, this processor can be the same as or separate from the ultrasound system's central controller. Also, the processor can be a single component in the ultrasound system or can be several components when its functionality is distributed to several components in the system. Further, the processor 810 of the ultrasound system 800 can be located external from an ultrasound system cart 800 that houses the beamformer 825, as shown in FIG. 8. In this alternate embodiment, the processor 810 can communicate with the components of the system located within the cart via a serial port or a video in/out connection, for example. This alternative embodiment finds particular use in situations in which the processor is an accessory to a pre-existing ultrasound system. Of course, both the processor and the beamformer can both be housed in the ultrasound system cart.

It is intended that the foregoing detailed description be understood as an illustration of selected forms that the invention can take and not as a definition of the invention. It is only the following claims, including all equivalents, that are intended to define the scope of this invention.

What is claimed is:

1. A method for configuring a medical diagnostic ultrasound imaging system, the method comprising:

(a) sending patient information from a hospital information system to an ultrasound system coupled to the hospital information system;

(b) with the ultrasound system, determining a set of ultrasound settings that are associated with the patient information sent from the hospital information system; and (c) automatically configuring the ultrasound system with the set of ultrasound settings determined in (b).

2. The method of claim 1 further comprising:

(d) with the ultrasound system, determining a set of patient demographic fields that are associated with the patient information sent from the hospital information system; and (e) automatically configuring a patient demographic worksheet with the patient demographic fields determined in (d).

3. The method of claim 2 further comprising:

(f) automatically populating at least some of the fields of the patient demographic worksheet with at least some of the patient information sent from the hospital information system.

4. The method of claim 1, wherein the ultrasound system comprises a set of ultrasound setting presets, and wherein (b) comprises selecting an ultrasound setting preset from the set of ultrasound setting presets by mapping the patient information sent from the hospital information system to the set of ultrasound setting presets.

5. The method of claim 4, wherein the act of mapping comprises one-to-one mapping.

6. The method of claim 4, wherein the act of mapping comprises using a pre-configured mapping table.

7. The method of claim 4, wherein the act of mapping comprises algorithmic mapping.

8. The method of claim 1, wherein patient information comprises patient demographic information.

9. The method of claim 1, wherein patient information comprises scheduled procedure step information.

10. The method of claim 9, wherein the scheduled procedure step information comprises a scheduled procedure step description field.

11. A method for configuring a medical diagnostic ultrasound imaging system, the method comprising:

(a) sending patient information from a hospital information system to an ultrasound system coupled to the hospital information system;

(b) with the ultrasound system, determining a plurality of suggested ultrasound settings that are associated with the patient information sent from the hospital information system;

(c) communicating the plurality of suggested ultrasound settings to a user of the ultrasound system;

(d) receiving a selection from the user of one of the plurality of suggested ultrasound settings; and (e) configuring the ultrasound system with the ultrasound settings associated with the selection received (d).

12. The method of claim 11 further comprising:

(f) with the ultrasound system, determining a set of patient demographic fields that are associated with the patient information sent from the hospital information system, and (g) automatically configuring a patient demographic worksheet with the patient demographic fields determined in (f).

13. The method of claim 12 further comprising:

(h) automatically populating at least some of the fields of the patient demographic worksheet with at least some of the patient information sent from the hospital information system.

14. The method of claim 11, wherein the ultrasound system comprises a set of ultrasound setting presets, and wherein (b) comprises determining a plurality of suggested ultrasound setting presets that are associated with the patient information sent from the hospital information system by mapping the patient information sent from the hospital information system to the set of ultrasound setting presets.

15. The method of claim 11, wherein patient information comprises patient demographic information.

16. The method of claim 11, wherein patient information comprises scheduled procedure step information.

17. A method for automatically configuring a patient demographic worksheet on a medical diagnostic ultrasound imaging system, the method comprising:
  (a) sending patient information from a hospital information system to an ultrasound system coupled to the hospital information system;
  (b) with the ultrasound system, determining a set of patient demographic fields that are associated with the patient information sent from the hospital information system; and
  (c) automatically configuring a patient demographic worksheet with the set of patient demographic fields determined in (b).

18. The method of claim 17 further comprising:
  (d) populating at least some of the fields of the patient demographic worksheet with at least some of the patient information sent from the hospital information system.

19. The method of claim 17, wherein the ultrasound system comprises a set of patient demographic worksheets, and wherein (b) comprises selecting a patient demographic worksheet from the set of patient demographic worksheets by mapping the patient information sent from the hospital information system to the set of patient demographic worksheets.

20. The method of claim 19, wherein the act of mapping comprises one-to-one mapping.

21. The method of claim 19, wherein the act of mapping comprises using a pre-configured mapping table.

22. The method of claim 19, wherein the act of mapping comprises algorithmic mapping.

23. The method of claim 17, wherein patient information comprises patient demographic information.

24. The method of claim 17, wherein patient information comprises scheduled procedure step information.

25. A method for automatically populating at least some fields of a patient demographic worksheet on a medical diagnostic ultrasound imaging system, the method comprising:
  (a) sending patient information from a hospital information system to an ultrasound system coupled to the hospital information system;
  (b) with the ultrasound system, determining a set of patient demographic data that is associated with the patient information sent from the hospital information system; and
  (c) automatically populating at least some of the fields of a patient demographic worksheet on the ultrasound system with at least some of the patient demographic data determined in (b).

26. The method of claim 25, wherein patient information comprises patient demographic information.

27. The method of claim 25, wherein patient information comprises scheduled procedure step information.

28. A medical diagnostic ultrasound imaging system adapted to be coupled with a hospital information system comprising patient information, the ultrasound imaging system comprising:
  a beamformer;
  a communications device; and
  a processor coupled with the beamformer and communications device, the processor receiving patient information from a hospital information system coupled with the communications device of the ultrasound system;
  wherein the processor is operative to determine a set of ultrasound settings that are associated with the patient information received from the hospital information system and to automatically configure the ultrasound system with the set of ultrasound settings.

29. The ultrasound imaging system of claim 28, wherein the communications device comprises a modem.

30. The ultrasound imaging system of claim 28, wherein the communications device comprises a network connector.

31. The ultrasound imaging system of claim 28 further comprising an ultrasound system cart and wherein the beamformer is housed within the ultrasound system cart and the processor is externally located from the ultrasound system cart.

32. The ultrasound imaging system of claim 28 further comprising an ultrasound system cart and wherein the beamformer and the processor are housed within the ultrasound system cart.

33. A medical diagnostic ultrasound imaging system adapted to be coupled with a hospital information system comprising patient information, the ultrasound imaging system comprising:
  a beamformer;
  a communications device; and
  a processor coupled with the beamformer and communications device, the processor receiving patient information from a hospital information system coupled with the communications device of the ultrasound system;
  wherein the processor is operative to determine a set of patient demographic fields that are associated with the patient information received from the hospital information system and to automatically configure a patient demographic worksheet on the ultrasound system with the set of patient demographic fields.

34. The ultrasound imaging system of claim 33, wherein the communications device comprises a modem.

35. The ultrasound imaging system of claim 33, wherein the communications device comprises a network connector.

36. The ultrasound imaging system of claim 33 further comprising an ultrasound system cart and wherein the beamformer is housed within the ultrasound system cart and the processor is externally located from the ultrasound system cart.

37. The ultrasound imaging system of claim 33 further comprising an ultrasound system cart and wherein the beamformer and the processor are housed within the ultrasound system cart.

38. A medical diagnostic ultrasound imaging system adapted to be coupled with a hospital information system comprising patient information, the ultrasound imaging system comprising:
  a beamformer;
  a communications device; and
  a processor coupled with the beamformer and communications device, the processor receiving patient information from a hospital information system coupled with the communications device of the ultrasound system;
  wherein the processor is operative to determine a plurality of suggested ultrasound settings that are associated with the patient information sent from the hospital information system and to configure the ultrasound system with one of the suggested ultrasound settings selected by a user of the ultrasound system.

39. The ultrasound imaging system of claim 38, wherein the communications device comprises a modem.

40. The ultrasound imaging system of claim 38, wherein the communications device comprises a network connector.

41. The ultrasound imaging system of claim 38 further comprising an ultrasound system cart and wherein the beamformer is housed within the ultrasound system cart and the processor is externally located from the ultrasound system cart.

42. The ultrasound imaging system of claim 38 further comprising an ultrasound system cart and wherein the beamformer and the processor are housed within the ultrasound system cart.

43. A medical diagnostic ultrasound imaging system adapted to be coupled with a hospital information system comprising patient information, the ultrasound imaging system comprising:

a beamformer;

a communications device; and a processor coupled with the beamformer and communications device, the processor receiving patient information from a hospital information system coupled with the communications device of the ultrasound system;

wherein the processor is operative to determine a set of patient demographic data that is associated with the patient information sent from the hospital information system and to automatically populate at least some of the fields of a patient demographic worksheet on the ultrasound system with at least some of the set of patient demographic data.

44. The ultrasound imaging system of claim 43, wherein the communications device comprises a modem.

45. The ultrasound imaging system of claim 43, wherein the communications device comprises a network connector.

46. The ultrasound imaging system of claim 43 further comprising an ultrasound system cart and wherein the beamformer is housed within the ultrasound system cart and the processor is externally located from the ultrasound system cart.

47. The ultrasound imaging system of claim 43 further comprising an ultrasound system cart and wherein the beamformer and the processor are housed within the ultrasound system cart.

* * * * *